United States Patent
Stark

(10) Patent No.: US 6,617,582 B2
(45) Date of Patent: Sep. 9, 2003

(54) SCINTILLATION CAMERA HAVING MULTIPLE FIELDS OF VIEW

(75) Inventor: Iain Stark, Manotick (CA)

(73) Assignee: IS2 Research Inc., Nepean (CA)

( * ) Notice: Subject to any disclaimer, the term of this patent is extended or adjusted under 35 U.S.C. 154(b) by 0 days.

(21) Appl. No.: 09/871,831

(22) Filed: Jun. 1, 2001

(65) Prior Publication Data

US 2002/0008204 A1 Jan. 24, 2002

Related U.S. Application Data

(63) Continuation-in-part of application No. 09/713,885, filed on Nov. 16, 2000.

(30) Foreign Application Priority Data

Jul. 21, 2000 (CA) .............................................. 2314205

(51) Int. Cl.[7] .............................................. G01T 1/166
(52) U.S. Cl. .............................. 250/363.05; 250/363.04
(58) Field of Search ...................... 250/363.05, 363.04, 250/363.02, 363.08, 363.09, 363.1, 362

(56) References Cited

U.S. PATENT DOCUMENTS

| | | | | |
|---|---|---|---|---|
| 5,206,512 A | * | 4/1993 | Iwao | 250/363.05 |
| 5,691,538 A | * | 11/1997 | Ohike et al. | 250/363.05 |
| 5,929,446 A | * | 7/1999 | Plummer et al. | 250/363.05 |
| 6,043,494 A | * | 3/2000 | Yamakawa et al. | 250/363.04 |
| 6,114,701 A | * | 9/2000 | Plummer et al. | 250/363.05 |
| 6,137,109 A | * | 10/2000 | Hayes | 250/363.05 |
| 6,180,943 B1 | * | 1/2001 | Lange | 250/363.05 |

* cited by examiner

Primary Examiner—Constantine Hannaher
Assistant Examiner—Otilia Gabor
(74) Attorney, Agent, or Firm—Pearne & Gordon LLP

(57) ABSTRACT

A scintillation camera using the dual scintillation detector head is disclosed. The scintillation camera can include two dual scintillation detector heads, which are fixed in opposition to each other. The camera can include a dual scintillation detector head and a single scintillation detector head, which are also fixed in opposed relation to each other. The dual scintillation detector head has two scintillation detectors, which are fixed relative to each other, preferably fixed substantially at 90 degrees to each other. Each scintillation detector has a plurality of photomultiplier tubes, a collimator, and a scintillation medium. The two scintillation detectors are housed in a L-shape rigid casing,

20 Claims, 5 Drawing Sheets

SCINTILLATION CAMERA HAVING MULTIPLE FIELDS OF VIEW

CROSS REFERENCE TO RELATED APPLICATION

This application is a continuation-in-part of Ser. No. 09/713,885, filed Nov. 16, 2000, which is incorporated herein by reference for all purposes.

FIELD OF THE INVENTION

The invention relates generally to scintillation cameras, and more particularly to an improved scintillation camera comprising a plurality of fields of view.

BACKGROUND OF THE INVENTION

Scintillation cameras are well known in the art of nuclear medicine, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator (a scintillation crystal) and an array of photomultiplier tubes. The gamma rays are directed to the scintillator which absorbs the radiation and produces, in response, a very small flash of light. The photodetectors, which are placed in optical communication with the scintillation crystal, convert these flashes into electrical signals which are subsequently processed. The SIGNAL processing enables the camera to produce an image of the distribution of the radioisotope within the patient.

Gamma radiation is emitted in all directions and it is necessary to collimate the radiation before the radiation impinges on the scintillation crystal. This is accomplished by a collimator which is a sheet of absorbing material, usually lead, perforated by relatively narrow channels. The collimator is detachably secured to the detector head, allowing the collimator to be changed to enable the detector head to be used with the different energies of isotope to suit particular characteristics of the patient study. The collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient A partial whole body view is simply a whole body view that covers only part of the body of the patient. In order to be able to achieve a whole body view, a gamma camera must be positionable at any location relative to a patient in an automated sequence of views The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image, In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Depending an the type of study being conducted, the configuration of the radiation detector is variable. The two common types of studies are planar imaging and cardiac imaging.

Planar imaging is used for bone scanning and various other types including liver scanning. In order to obtain optimum images, two cameras should be opposed one another. In general, these cameras should also be relatively large in order to obtain a large field of view.

Cardiac imaging is used for obtaining images of the heart. In order to obtain optimum images, two detector heads and two collimators should be at substantially 90 degrees to one another; with their fields of view as close as possible.

In an attempt to provide the ability to produce both types of images with a single scintillation camera, detectors of variable geometry were developed. These systems conduct both planar and cardiac imaging However, the problem with these systems is that it is difficult, if not impossible, to position the heads to the exact same position where a prior image was taken from. This is primarily due to backlash in the mechanical structure of the system. When the computer conducts the reconstruction of the images, it does so with the assumption that the information it is writing into the pixels in the image display is in the correct place. With the presence of backlash, the computer is unknowingly writing information into the wrong place, which results in blurring of the image and loss of image resolution. This in turn results in images that are inaccurate. This also precludes any reproducibility of the study.

Also, these systems use two separate and distinct detectors to produce the 90 degrees view. This means that it further requires lead shielding between the detectors to prevent any stray radiation from getting into each of the detectors With the lead shielding between the detectors, the detectors are prevented from being as close together as possible in the 90 degree position; they are not as close as they would be without the shielding between them. Since then, the fields of view of the detectors are not close as desired, this leaves open the risk of cutting off views of the heart as cardiac imaging is conducted.

These systems also, generally, cannot easily vary in size of support to accommodate different sizes of patients. In order to accommodate either a larger or smaller patient, the entire scintillation camera must be physically repositioned.

The use of three detectors is known, but usually, these systems use three relatively small detectors in the viewing area. The smaller fields of view of the detectors mean they cannot produce whole body images or images of the skeleton.

Even if the system did utilize relatively large detectors, systems using three relatively large detectors have disadvantages. The detectors are generally set at 60 degrees from one another, and when large detectors are placed in this configuration, the distance from the detector head to the patient is undesirably large. To overcome this, the detectors are required to slide over one another. As well, a 60 degrees setting is not ideal for cardiac work. As mentioned above, the image should be taken at 90 degrees.

Therefore, there is a need for a scintillation camera with a great versatility, which can be used for both planar and cardiac imaging, and can mitigate the problems and disadvantages of the prior art camera.

SUMMARY OF THE INVENTION

According to one aspect of the invention, there is provided a scintillation camera having at least one dual scintillation detector head. The scintillation camera comprises (a) a first scintillation detector head, the first scintillation detector head being a dual scintillation detector head which comprises two scintillation detectors fixed relative to each other in the form of V-shape, (b) a second scintillation detector head spaced from the first scintillation detector head such that a portion of a patient's body may be placed in the fields of view provided by at least the first scintillation detector head, and (c) a mechanism for supporting the first and second scintillation detector heads in selected positions relative to each other and to the portion of the patient's body when in use. The supporting mechanism is adapted to position the first and second scintillation detector heads such that a portion of a patient's body may be located between the first and second scintillation detector heads.

The second scintillation detector head preferably includes a dual scintillation detector head or a single scintillation detector head. In the dual scintillation detector head, the two scintillation detectors are substantially at 90 degrees to each other.

The supporting mechanism preferably comprises an annular support defining at the center thereof a patient cylinder where the patient is positioned along the longitudinal axis of the patient cylinder, and a pair of mounding structures for mounting the first and second scintillation detector heads on the annular support. The annular support can be rotatable about the longitudinal axis of the patient cylinder. The first and second scintillation detector heads are rotatably supported by the mounting structures about two individual supporting axes respectively, which are vertical to the longitudinal axis of the patient cylinder. The two supporting axes are parallel to each other.

The first and second scintillation detector heads are preferably supported on the annular support in opposed relation to each other, typically, in symmetrically opposed relation to each other.

BRIEF DESCRIPTION OF THE DRAWINGS

Other aspects and advantages of the invention, as well as the structure and operation of various embodiments of the invention, will become apparent to those ordinarily skilled in the art upon review of the following description of the invention in conjunction with the accompanying drawings, in which;

FIG. 1b is a frontal sectional view showing the inside configuration of the dual detector head in FIG. 1a;

FIG. 2b is a front elevation view of the scintillation camera of FIG. 2a;

FIG. 2c is a front elevation view illustrating one possible position of the dual detector head of the scintillation camera in FIG. 2a.

DETAILED DESCRIPTION OF THE PREFERRED EMBODIMENTS

Figure 1A:
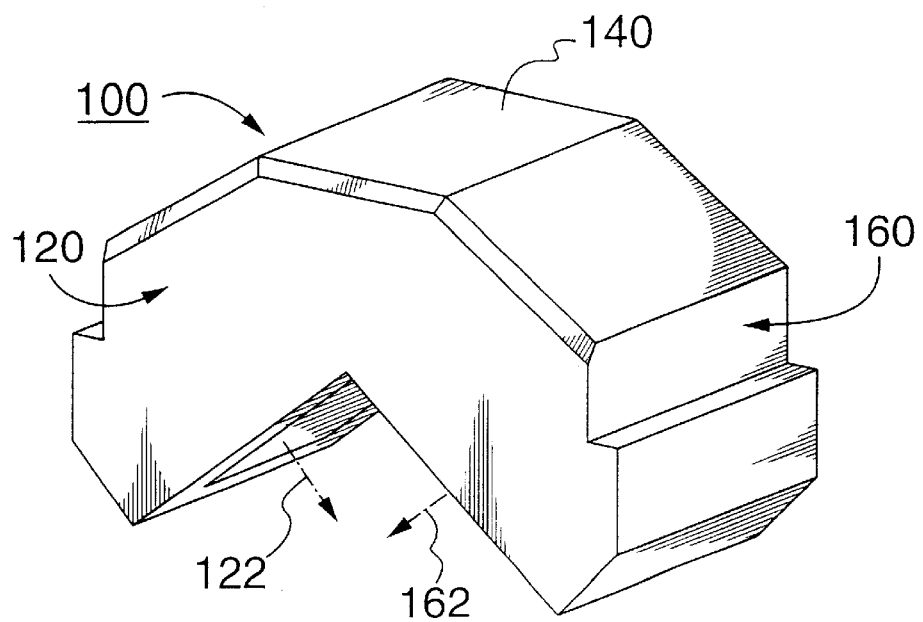
FIG. 1a is a perspective view of a dual detector head comprising two detector heads at 90 degree to each other.
Figure 1B:
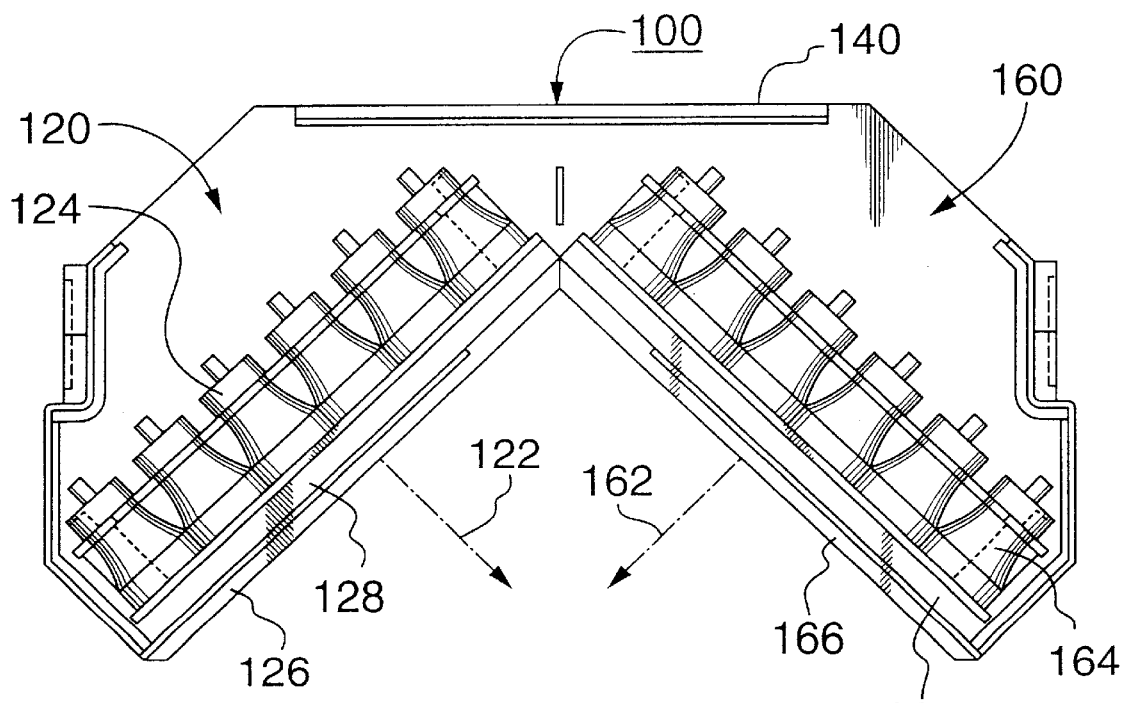

In FIGS. 1a and 1b, there is shown a dual scintillation detector head according to one embodiment of the present invention, which is generally denoted by reference numeral 100. As illustrated, the dual scintillation detector head 100 (hereinafter, a dual detector head) comprises two scintillation detectors 120 and 160 (hereinafter, a detector), and a housing 140 containing the two detectors. The housing 140 is an L-shaped rigid casing wherein the two detectors 120 and 160 are firmly fixed relative to each other. The detectors 120 and 160 include arrays of photomultiplier tubes 124 and 164, collimator plates 126 and 166, and scintillation crystals 128 and 168 respectively. Also, the detectors 120 and 160 provide their own fields of view 122 and 162 respectively.

The two detectors 120 and 160 in the dual detector head 100 are fixed at substantially 90 degrees to each other, and therefore, the two collimator plates 126 and 166 are also substantially at 90 degrees to each other, so that stray radiation can be prevented from entering either collimator (it being noted here that the collimator holes or channels extend normal to the surfaces of the respective collimator plates). This eliminates the requirement for lead shielding between them as in the prior art cameras. Without the lead shielding, therefore, the fields of view 122 and 162 of the dual detector head 100 can be closer together, resulting in a minimized risk of cutting off views during operation. Also the rigid support structure allows the two detector heads 120 and 160 to be repositioned easily to an original position. This allows reproducibility of studies. Those skilled in the art will realize that the dual detector head 100 shown in FIGS. 1a and 1b is of an ideal geometry for cardiac studies.

Figure 2A:
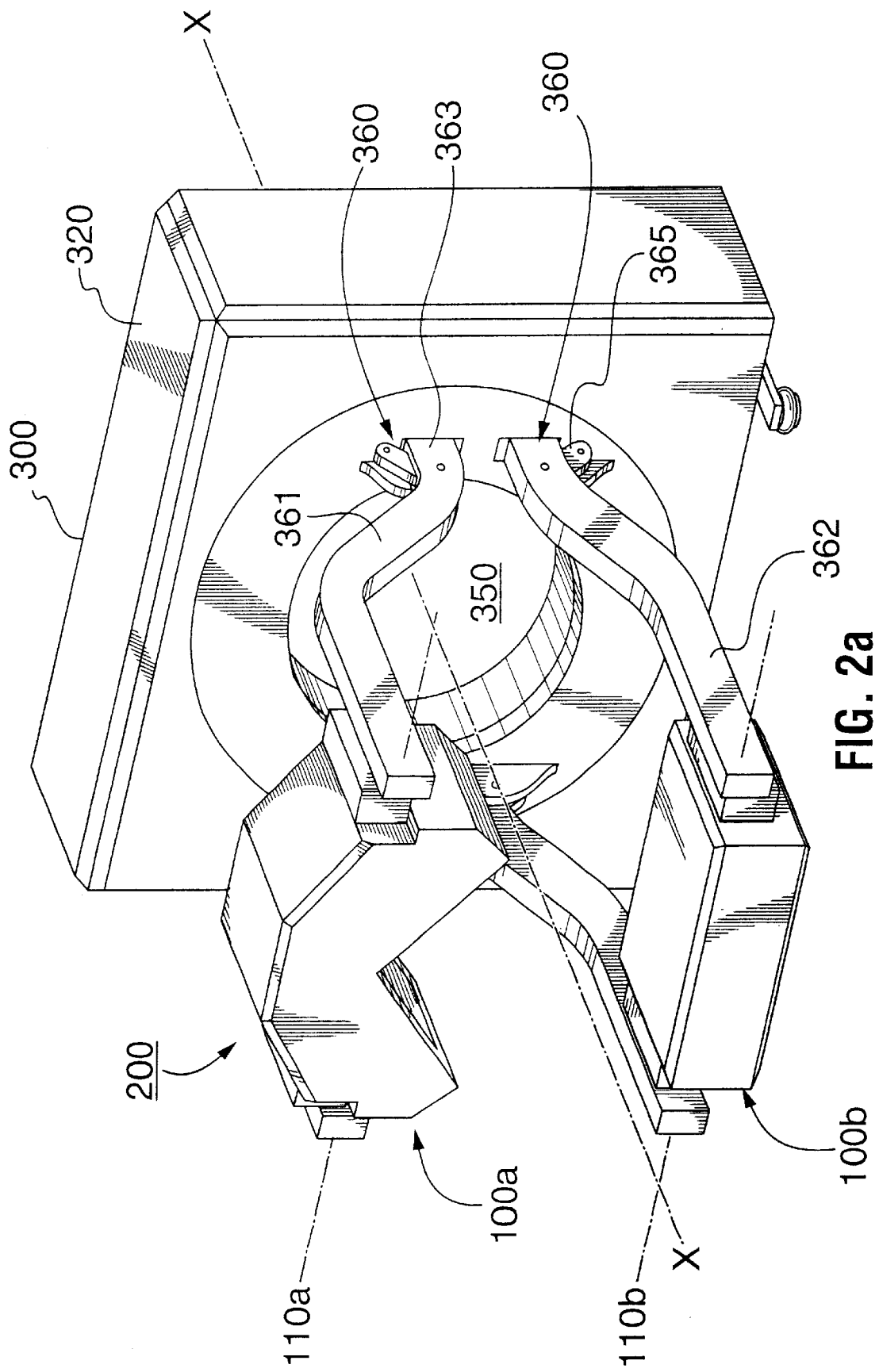
FIG. 2a is a perspective view of a scintillation camera using the dual detector head of FIG. 1 according to one embodiment of the invention.
Figure 2B:
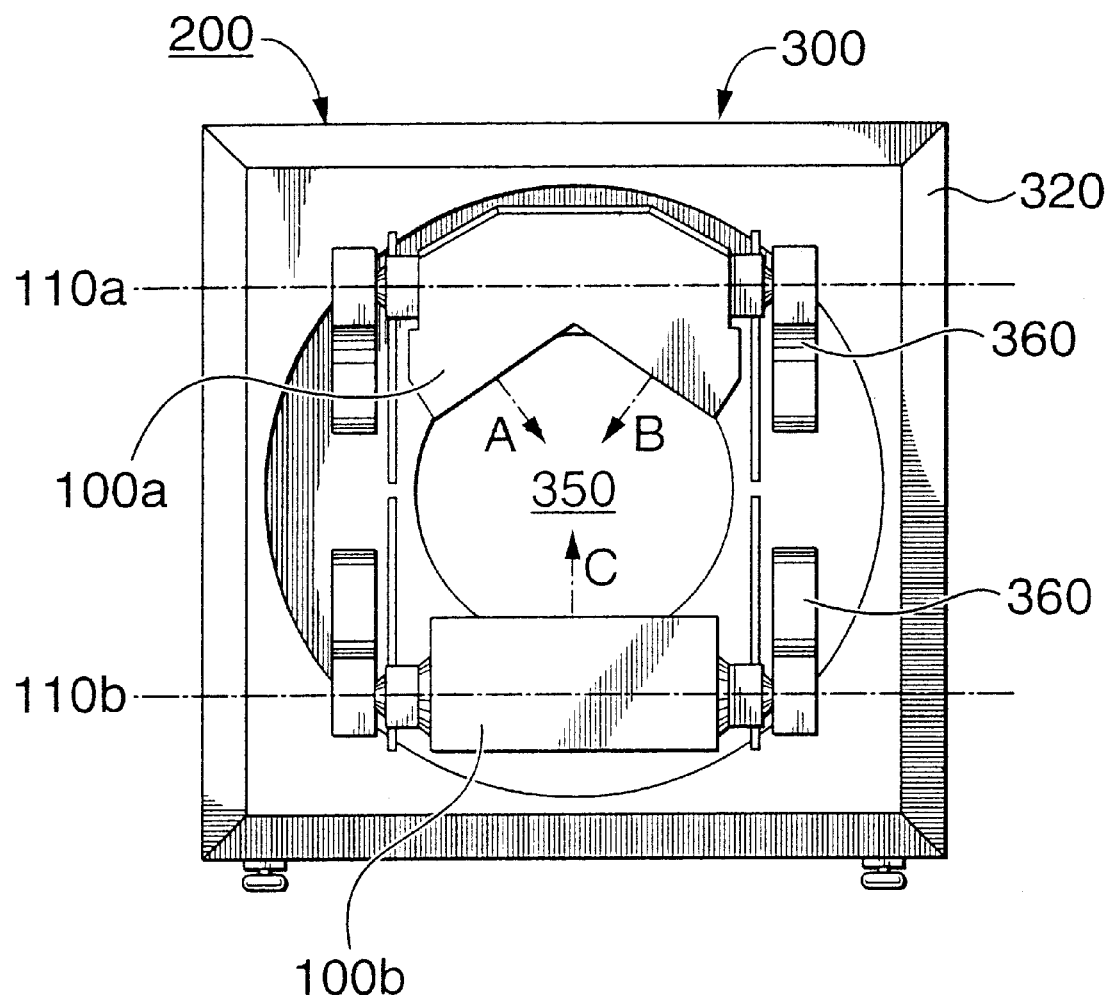

FIGS. 2a and 2b depict an embodiment of a scintillation camera using a dual detector head, which is generally denoted by a reference numeral 200. FIG. 2b shows a front elevation view of FIG. 2a. As illustrated, in this embodiment, the scintillation camera 200 includes one dual detector head 100a and one single scintillation detector head 100b (hereinafter, a single detector head). The detector heads 100a and 100b are fixed in opposition to each other as depicted in FIG. 2b. During the operation of the camera, therefore, the spatial relationship among their fields of view is fixed such that clearer images can be provided.

As shown in FIGS. 2a and 2b, the detector heads 100a and 100b are supported and driven by a supporting and driving mechanism 300, such that the supporting axis 110a of the dual head 100a remains parallel to the support axis 110b of the single head 100b during operation. The supporting and driving mechanism will be described hereafter.

The embodiment of FIGS. 2a and 2b provides a great of versatility. That is, it gives three fields of view A, B, and C, and takes pictures from three directions at the same time. The images from those three directions taken at the same time is very useful for other organ studies, including liver, brain, lungs, kidneys, and bones. Further, the dual detector head 100a can be used for cardiac imaging simultaneously while the single detector head 100b may be used for a whole body imaging.

Figure 3:
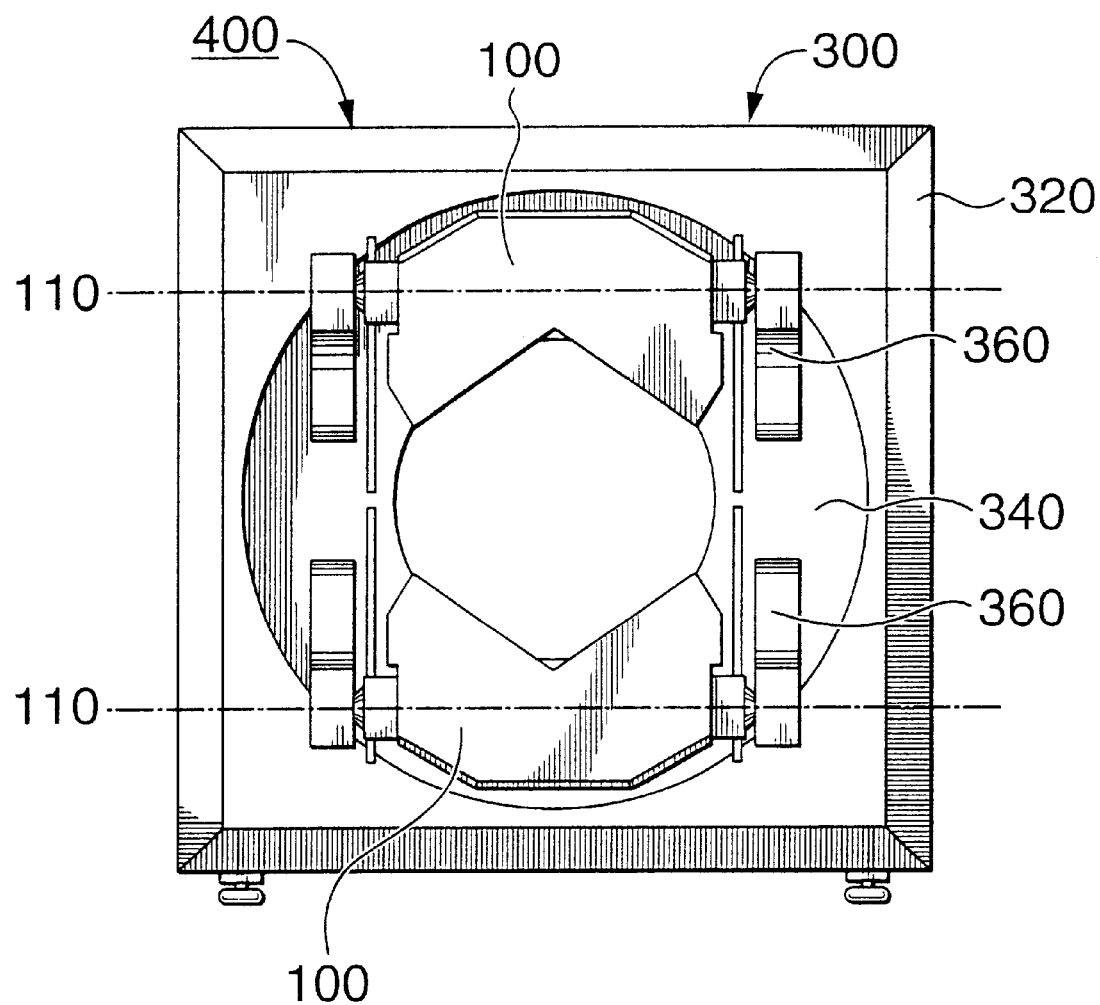
FIG. 3 is a front elevation view of a scintillation camera using two dual detector heads according to another embodiment of the invention.

In FIG. 3, there is illustrated another embodiment of a scintillation camera 400 in accordance with the present invention. In this embodiment, the camera 400 includes two dual detector heads 100, each head 100 having the structure described. Similarly, these two dual detector heads 100 are fixed in opposed spaced relation to each other, preferably, in exact symmetrical relation with each other, such that the horizontal supporting axes 110 of the heads are parallel to each other. Therefore, the spatial relationship among their fields of view remains fixed all the time during the operation of the camera such that clearer images can be taken.

The scintillation camera 400 in FIG. 3 provides four fields of view and is, therefore, particularly suited for brain imaging. Conventionally, there has been no satisfactorily suitable tool for brain imaging, but the configuration of this embodiment provides enough sensitivity and enough image quality for brain imaging so that it can be very useful for diagnosing depression, schizophrenia, Alzheimer's and other brain disorders.

Figure 2C:
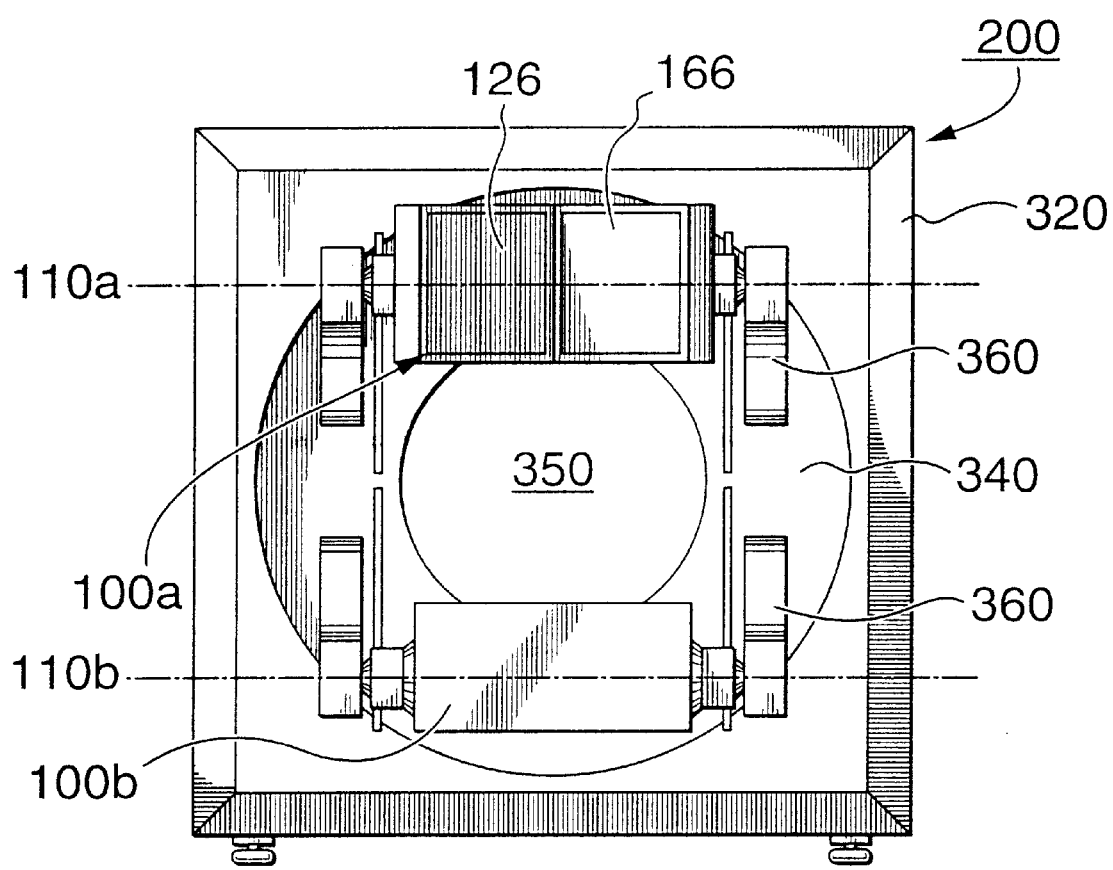

The supporting and driving mechanism 300 of the scintillation camera 200 and 400 will be described below. As illustrated in FIGS. 2 and 3, the mechanism 300 for the dual detector heads includes a base 320, and an annular support 340 rotatably supported in the base 320 by suitable bearings and connected to a motor drive (not shown) The annular support 340 defines a "patient cylinder" 350 defining an axis x along which the patient extend when the equipment is in use. A mounting structure 360 for mounting the detector heads on the annular support 340 comprise spaced pairs of upper and lower support arms 361 and 362 as shown in FIG. 2a. The upper support arms 361 engage opposing ends of the dual detector head 100a and permit limited rotation of the dual detector head 100a relative to support arms 361 about the support axis 110a. The lower support arms 362 engage opposing ends of the single detector head 100b and permit limited rotation of the single detector head 100b relative to support arms 362 about the support axis 110b. The opposing ends of the upper and lower support arms 361 and 362 are secured to the annular support 340 via mounting mechanisms 363 and 365. During the operation of the camera, a stretcher, on which a patient lies, will be placed in the patient cylinder 350. By rotating the annular support 340, the detector heads can be moved around the patient, taking pictures at various angles relative to the patient. The mounting structure 360 is designed for moving the detector heads toward and away from the patient, and rotating them about the supporting axes 110a and 110b thereof relative to the support structure and the patient as shown in FIG. 2c. Further, the driving mechanism is designed for precisely positioning the detector heads repeatedly at the same point relative to the patient. Various mechanisms of this type are known to those skilled in the art. For example, U.S. patent applications Ser. Nos. 09/127,982 and 09/127,989, which are filed Aug. 3, 1998 by the present inventor entitled "Positioner for a scintillation camera detector head," and "Support structure for medical diagnostic equipment" respectively, disclose suitable supporting and driving mechanisms for the scintillation cameras, and the disclosures of these applications are incorporated herein by reference thereto.

By using the mounting structure 360 of the mechanism 300, the dual detector heads in the cameras of FIGS. 2 and 3 can be rotated about the supporting axes 110, 110a, and 110b, as the case may be to allow them to face their fields of view (as defined by their collimator plates) out. FIG. 3 shows the detector heads rotated so as to face outwardly. Therefore, the cameras aim at the heart of a patient, who may be standing or riding an exercise bicycle, such that it can take successive pictures or images of the patient's heart behaviour under these conditions.

The invention allows for a great degree of flexibility in the configuration of the cameras and the ability to upgrade. For example, the cameras 200, 400 as shown can use the same mounting structure 360 for both the dual detector head and the single detector head such that the single detector head can be replaced with the dual detector head if desired. Therefore, the structure provides for various combinations of the dual head and single head detectors to be used according to the field of study.

While the invention has been described according to what is presently considered to be the most practical and preferred embodiments, it must be understood that the invention is not limited to the disclosed embodiments. Those ordinarily skilled in the art will understand that various modifications and equivalent structures and functions may be made without departing from the spirit and scope of the invention as defined in the claims. Therefore, the invention as defined in the claims must be accorded the broadest possible interpretation so as to encompass all such modifications and equivalent structures and functions.

What is claimed is:

1. A scintillation camera comprising:
   a first scintillation detector head, the first scintillation detector head being a dual scintillation detector head which comprises two scintillation detectors fixed relative to each other in the form of V-shape, the two scintillation detectors providing first and second fields of view;
   a second scintillation detector head including a scintillation detector which provides a third field of view; and
   a mechanism for supporting the first and second scintillation detector heads in selected positions relative to each other and to the portion of a patient's body when in use, the mechanism including a first rotatable mechanism and a second rotatable mechanism,
   the first rotatable mechanism rotating the first and second scintillation detector heads about a first axis so as to maintain a spatial relationship among the first, second and third field of views,
   the second rotatable mechanism rotating the first and second scintillation detector heads about a second axis, which is different from the first axis.

2. A scintillation camera according to claim 1, wherein the supporting mechanism is adapted to position the first and second detector heads such that a portion of a patient's body may be located between the first and second scintillation detector heads.

3. A scintillation camera according to claim 2, wherein the second scintillation detector head comprises a dual scintillation detector head.

4. A scintillation camera according to claim 2, wherein the second scintillation detector head includes a single scintillation detector head.

5. A scintillation camera according to claim 2, wherein the first and second scintillation detector heads are supported by the supporting mechanism in opposed relation to each other.

6. A scintillation camera according to claim 5, wherein the first and second scintillation detector heads are supported by the supporting mechanism in symmetrically opposed relation to each other.

7. A scintillation camera according to claim 1, wherein the first rotatable mechanism includes an annular support defining at the center thereof a patient cylinder where the patient is positioned along the longitudinal axis of the patient cylinder, the annular support being rotatable about the longitudinal axis of the patient cylinder.

8. A scintillation camera according to claim 7, wherein the first rotatable mechanism further includes first and second supporting axes extending from the annular support in a direction of the longitudinal axis of the patient cylinder and being parallel to each other, the first and second scintillation detector heads being mounted on the annular support through the first and second supporting axes respectively.

9. A scintillation camera according to claim 7, wherein the second scintillation detector head includes a dual scintillation detector head.

10. A scintillation camera according to claim 7, wherein the second scintillation detector head includes a single scintillation detector head.

11. A scintillation camera according to claim 7, wherein the first and second scintillation detector heads are supported on the annular support in opposed relation to each other.

12. A scintillation camera according to claim 11, wherein the first and second scintillation detector heads are supported on the annular support in symmetrically opposed relation to each other.

13. A scintillation camera according to claim 7, wherein the first rotatable mechanism further includes first and second supporting axes extending from the annular support in a direction of the longitudinal axis of the patient cylinder, the first and second scintillation detector heads being mounted on the annular support through the first and second supporting axes respectively.

14. A scintillation camera according to claim 13, wherein the second rotatable mechanism includes first and second rotatable devices, the first and second scintillation detector heads being rotatably attached to the first and second supporting axes through the first and second rotatable devices respectively.

15. A scintillation camera according to claim 7, wherein the supporting mechanism further includes first and second movable devices, the first and second mounting devices allowing the first and second scintillation detector heads to move toward and away from the center of the patient cylinder respectively.

16. A scintillation camera according to claim 1, wherein the two scintillation detectors are substantially at 90 degrees to each other.

17. A scintillation camera according to claim 1, wherein the first axis is substantially vertical to the second axis.

18. A scintillation camera according to claim 1, wherein the first rotatable mechanism includes a supporting device extending in a direction vertical to the rotation provided by the first rotatable mechanism, the first and second scintillation detector heads being mounted to the first rotatable mechanism through the supporting device.

19. A scintillation camera according to claim 18, wherein the first and second scintillation detector heads are connected to the supporting device through the second rotatable mechanism.

20. A scintillation camera according to claim 18, further comprising a movable mechanism for allowing the first and second detector heads to be movable.

* * * * *

UNITED STATES PATENT AND TRADEMARK OFFICE
CERTIFICATE OF CORRECTION

PATENT NO.     : 6,617,582 B2                                        Page 1 of 1
DATED          : September 9, 2003
INVENTOR(S)    : Iain Stark It is certified that error appears in the above-identified patent and that said Letters Patent is hereby corrected as shown below:

<u>Title page,</u>
Item [*] Notice, please delete "by 0 days", and insert therefor -- by 105 days --.

<u>Column 1,</u>
Line 25, after "crystal", please insert -- , --.
Line 67, after "patient", please insert -- . --.

<u>Column 2,</u>
Line 12, please delete ",", and insert therefor -- . --.
Line 18, after "patient", please insert -- . --.
Line 31, please delete "an", and insert therefor -- on --.
Line 43, please delete ";", and insert therefor -- , --.
Line 47, after "imaging", please insert -- . --.
Line 65, after the first occurrence of "detectors", please insert -- . --.

<u>Column 5,</u>
Line 40, after "(not shown)", please insert -- . --.

<u>Column 8,</u>
Line 27, please delete "to", and insert therefor -- on --.
Line 35, after "second", please insert -- scintillation --.

Signed and Sealed this

Twentieth Day of January, 2004

JON W. DUDAS
*Acting Director of the United States Patent and Trademark Office*